United States Patent [19]
Taniguchi et al.

[11] Patent Number: 4,582,201
[45] Date of Patent: Apr. 15, 1986

[54] PRODUCT TRANSPORTING APPARATUS

[75] Inventors: Shin ichi Taniguchi, Osaka; Haruo Tsuji, Izumi, both of Japan

[73] Assignee: Takeda Chemical Industries, Ltd., Osaka, Japan

[21] Appl. No.: 585,581

[22] Filed: Mar. 2, 1984

[30] Foreign Application Priority Data

Nov. 26, 1983 [JP]  Japan .................. 58-222712

[51] Int. Cl.⁴ .................................................. B07C 5/00
[52] U.S. Cl. .................................. 209/587; 209/701; 209/937; 198/377; 198/471.1
[58] Field of Search ............... 198/689, 480, 478, 377, 198/471.1, 474.1; 209/701, 439, 538, 587

[56] References Cited

U.S. PATENT DOCUMENTS

| | | | |
|---|---|---|---|
| 2,427,712 | 9/1947 | Casler et al. | 198/689 X |
| 2,864,281 | 12/1958 | Draper | 198/377 X |
| 3,026,989 | 3/1962 | Schaltegger | 198/689 X |
| 3,528,544 | 9/1970 | Noguchi et al. | 209/701 |
| 3,756,402 | 9/1973 | Wagers, Jr. et al. | 209/587 X |
| 3,757,943 | 9/1973 | Chae et al. | 209/701 X |
| 3,811,567 | 5/1974 | Tomita et al. | 209/939 X |
| 3,834,522 | 9/1974 | Jackson | 198/689 X |
| 3,841,687 | 10/1974 | Banyas et al. | 198/689 X |
| 3,889,591 | 6/1975 | Noguchi | 198/689 |
| 3,920,541 | 11/1975 | Vandenberg et al. | 209/587 |
| 3,957,152 | 5/1976 | Heitmann | 198/480 |
| 4,129,206 | 12/1978 | Talbott | 198/651 X |
| 4,158,625 | 6/1979 | Takahashi et al. | 209/538 X |
| 4,354,602 | 10/1982 | Miyoshi et al. | 209/701 X |

Primary Examiner—Joseph E. Valenza
Assistant Examiner—Michael Stone
Attorney, Agent, or Firm—Wenderoth, Lind & Ponack

[57] ABSTRACT

A product transporting apparatus for transporting solid products of generally similar shape and/or size successively from a take-in station towards a take-out station, which has first and second rotary drums rotatable in the opposite directions to each other. The first and second rotary drums are of identical construction each having at least one circumferential row of tubular receptacles protruding radially outwardly from the outer periphery of the respective drum and circumferentially equally spaced from each other. The products can be successively supplied onto the first rotary drum and held by suction in position on the tubular receptacles then communicated with a vacuum source at the take-in station, which are in turn transported, during the rotation of the drums, to the transfer station where they are released from the receptacles on the first drum then communicated with a compressed air source, onto the respective tubular receptacles on the second rotary drum then communicated with the vacuum source. The products so transferred onto the second rotary drum are then transported in a similar fashion towards the take-out station where they are successively released from the second rotary drum onto a subsequent processing station.

4 Claims, 46 Drawing Figures

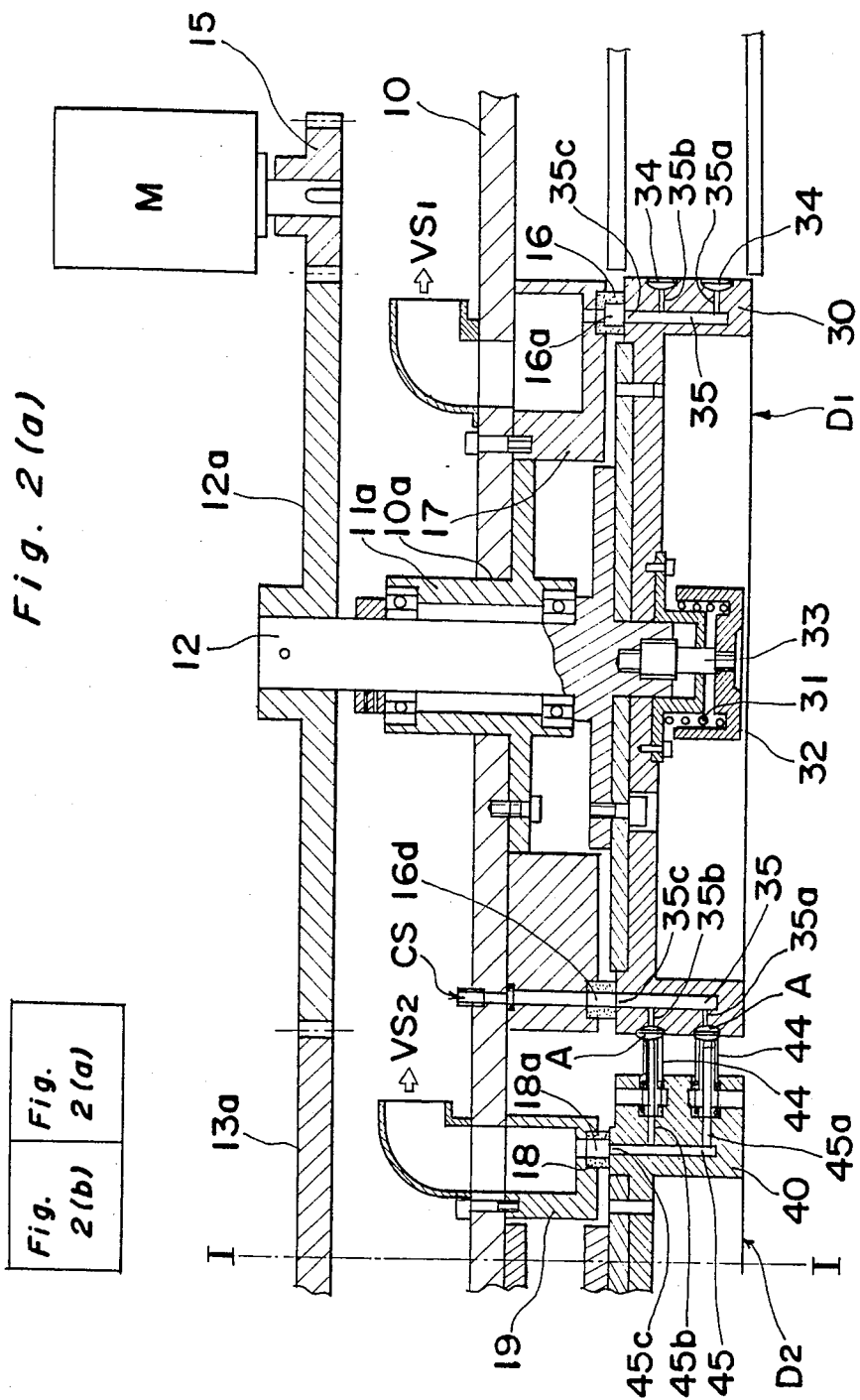

Fig. 15
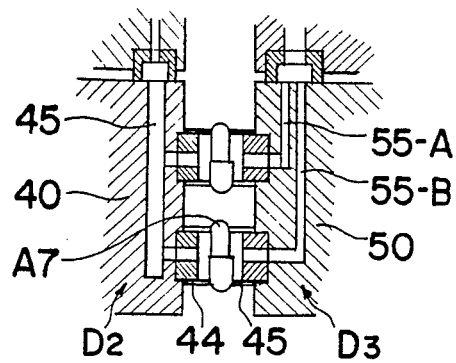
Fig. 16
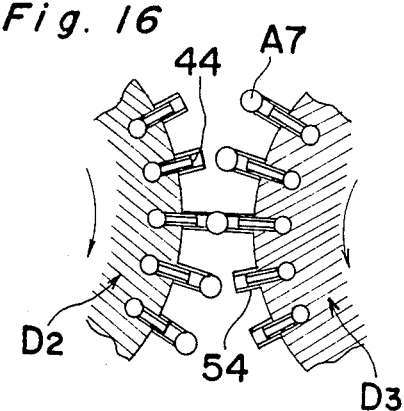
Fig. 17(a)    Fig. 17(b)    Fig. 17(c)
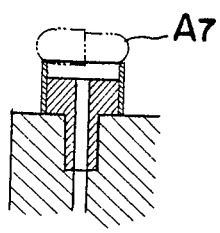 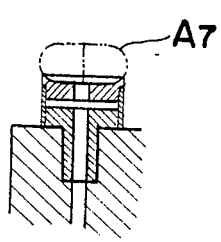 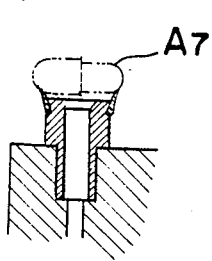
Fig. 18(a)    Fig. 18(b)
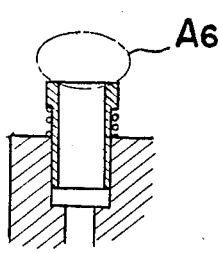 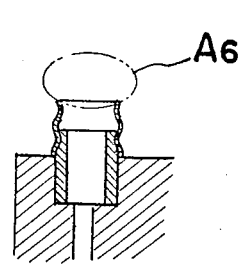
Fig. 19(b)    Fig. 19(b)
Fig. 19(c)    Fig. 19(d)
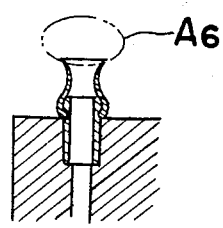 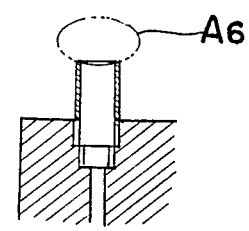

PRODUCT TRANSPORTING APPARATUS

BACKGROUND OF THE INVENTION

The present invention relates to a product transporting apparatus of a type capable of transporting products successively from one station to another while they are received in and retained by respective tubular receptacles on a rotary drum which are communicated with a source of vacuum.

The U.S. Pat. No. 3,889,591, patented June 17, 1975, discloses the use of a product transporting apparatus in a printing machine for automatically printing indicia on the opposite surfaces of tablets, pills, candies or any other solid products of any similar shape and/or size. The product transporting apparatus disclosed therein comprises first and second rotary drums of identical construction each having on its outer peripheral surface at least one circumferential row of radially inwardly recessed pockets arranged in circumferentially equally spaced relation to each other. While the first and second rotary drums are adapted to be driven in the opposite directions with respect to each other, the first rotary drum transports the products successively from a take-in position across a first printing station towards a transfer position where each of the pockets on the first rotary drum is lined up with that on the second rotary drum for the transfer of the respective product from the first rotary drum onto the second rotary drum, and the second rotary drum transports the products, which have been transferred one by one from the first rotary drum, from the transfer position across a second printing station towards the take-out position.

The apparatus also comprises means for permitting some of the pockets to be communicated with the vacuum source for enabling the products to be sucked into and received in the corresponding pockets, and means for permitting the pockets to be successively communicated with a source of compressed air during the continued rotation of the rotary drum to enable the products so transported to be ejected onto a subsequent processing station at the take-out station. This U.S. patent also disclose an idea of centering, i.e., correctly positioning, each product within the associated pocket by allowing it to float in air by the effect of a blast of compressed air when the pocket carrying the product arrives, during the rotation of one of the rotary drums, at a top position immediately above the drive shaft of the associated rotary drum.

SUMMARY OF THE INVENTION

The present invention is intended to provide an improved product transporting apparatus which is effective to transport the products successively from one station to another without each of the products being crushed between the rotary drums nor damaged in contact with one or both of the rotary drums.

Another object of the present invention is to provide an improved product transporting apparatus wherein, in the event that the apparatus is used so as to form a part of the product inspecting machine, the entire surface of each of the products being transported from one station to another can be monitored by a television camera.

In order to accomplish these and other objects of the present invention, the present invention contemplates the use of tubular receptacles which project radially outwardly from the outer periphery of each of the rotary drums, in contrast to the radially inwardly recessed pockets employed in the prior art apparatus of a similar kind. Each of the tubular receptacles comprises an inner tube made of rigid material and supported by the associated drum and an outer tube made of an elastic and soft material and mounted on the respective inner tube so as to project outwardly from the periphery of the associated drum.

In another aspect of the present invention, means is provided for spinning the tubular receptacles on each of the rotary drums about their own longitudinal axes. This spinning means is comprises of at least one friction band adapted to be frictionally engaged with the inner tube. For this purpose, the inner tube of each of the tubular receptacles on any one of the rotary drums is rotatably, but axially non-displaceably mounted on the associated rotary drum.

BRIEF DESCRIPTION OF THE DRAWINGS

This and other objects and features of the present invention will become apparent from the following description taken in conjunction with a preferred embodiment thereof with reference to the accompanying drawings, in which:

FIG. 15 is a sectional view showing the transfer of the product from the intermediate drum onto the delivery drum when the products are in the form of capsules;

FIG. 16 is a side sectional view of FIG. 15;

FIGS. 17(a) to 17(c) are schematic sectional views of a portion of either one of the intermediate and delivery drums showing different structures of tubular receptacles which may be employed in the practice of the present invention;

FIGS. 18(a) and 18(b) are perspective views of a portion of either one of the intermediate and delivery drums showing different structures of tubular receptacles which may be employed in the practice of the present invention when the products to be processed are capsules;

FIGS. 19(a) to 19(d) are schematic sectional views of a portion of either one of the intermediate and delivery drums showing different structures of the tubular receptacles which can be employed in the practice of the present invention;

DETAILED DESCRIPTION OF THE EMBODIMENT

Figure 1:
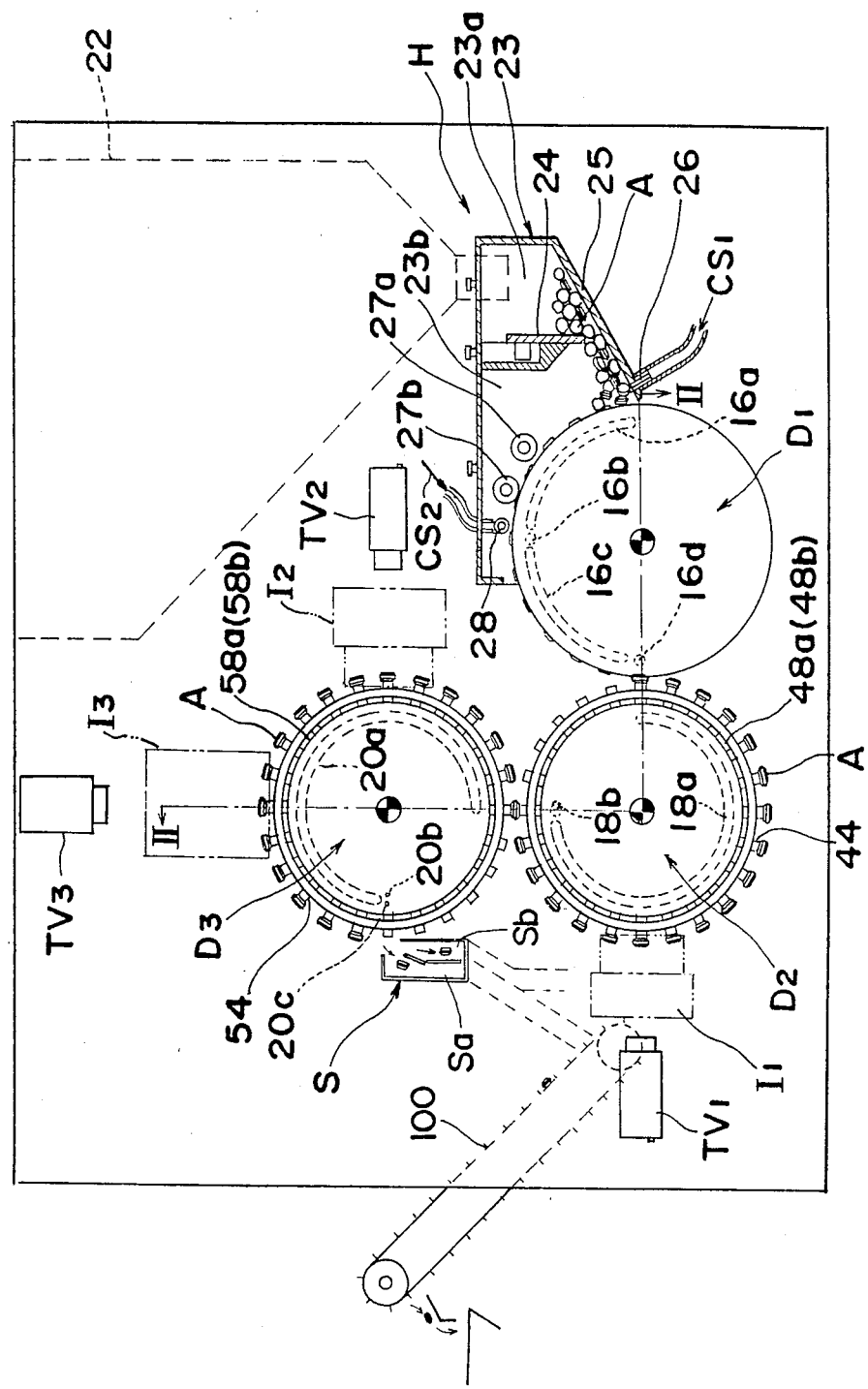
FIG. 1 is a schematic front view, with a portion broken away, of a product transporting apparatus utilizing a hopper assembly according to the present invention.

Before the description of the present invention proceeds, it is to be noted that like parts are designated by like reference numerals throughout the accompanying drawings.

Referring first to FIG. 1, a product transporting apparatus embodying the present invention is so designed as to transport solid products A of similar shape and/or size, each having a continuous and generally smooth surface, successively from a supply station towards a sorting station via first and second transfer stations. The apparatus will be described as forming a part of the product inspecting machine for inspecting the products as to the presence of any flaw and, therefore, the products A are successively passed across a first inspecting zone during the transportation thereof from the first transfer station towards the second transfer station and also across second and third inspecting zones during the transportation thereof from the second transfer station towards the sorting station. The first inspecting zone is provided with an illuminator unit I1 and a first television camera TV1 for inspecting one surface area of each of the products A being transported; the second inspecting zone is provided with an illuminator unit I2 and a second television camera TV2 for inspecting the opposite surface area of the respective product; and the third inspecting zone is provided with an illuminator unit I3 and a third television camera TV3 for inspecting the peripheral face of the respective product A.

The apparatus generally comprises a supply hopper assembly H, positioned at the supply station and adapted to receive a mass of the solid products A; a supply drum D1 rotatable in one direction, for example, in a counterclockwise direction for transporting the products A successively from the supply station towards the first transfer station; an intermediate drum D2 rotatable in a direction, counter to the direction of rotation of the supply drum D1, for transporting the products, which have been transferred one by one from the supply drum D1 at the first transfer station, towards the second transfer station past the first inspecting zone; a delivery drum D3 rotatable in the same direction as the supply drum D1 for transporting the products A, which have been transferred one by one from the intermediate drum D2 at the second transfer station, towards the sorting station first past the second inspecting zone and then past the third inspecting zone; and a sorting box S positioned at the sorting station and adjacent the delivery drum D3 for sorting the products A so transported to the sorting station into acceptable and rejected ones according to the result of inspection done at any one of the first, second and third inspecting zones. There constituent units H, D1, D2, D3, I1, TV1, I2, TV2, I3, TV3 and S are supported by a common upright support plate 10 having, as shown in FIG. 2, three bores 10a, 10b and 10c defined therein, the bore 10a being positioned laterally of the bore 10b which is positioned immediately below the bore 10c.

As shown in FIG. 2, the support plate 10 carries bearing sleeves 11a, 11b and 11c flanged rigidly thereto and extending through the bores 10a, 10b and 10c for the support of shafts 12, 13 and 14, respectively, on which the associated drums D1, D2 and D3 are mounted for rotation together therewith. On one side of the support plate 10 opposite to the drums D1 to D3, gear wheels 12a, 13a and 14a are rigidly mounted on the respective shafts 12, 13 and 14 for rotation together therewith, the gear wheel 14a being drivingly meshed with the gear wheel 13a which is in turn drivingly meshed with the gear wheel 12a meshed drivingly with a drive gear 15 on a drive shaft of an electric motor M. Thus, it will readily be seen that, during the operation of the motor M, the supply end delivery drums D1 and D3 can be rotated in the same direction, i.e., in the counterclockwise direction as viewed in FIG. 1, and the intermediate drum D2 can be rotated in a direction counter to the direction of rotation of any one of the supply and delivery drums D1 and D3, i.e., in the clockwise direction.

Figure 2B:
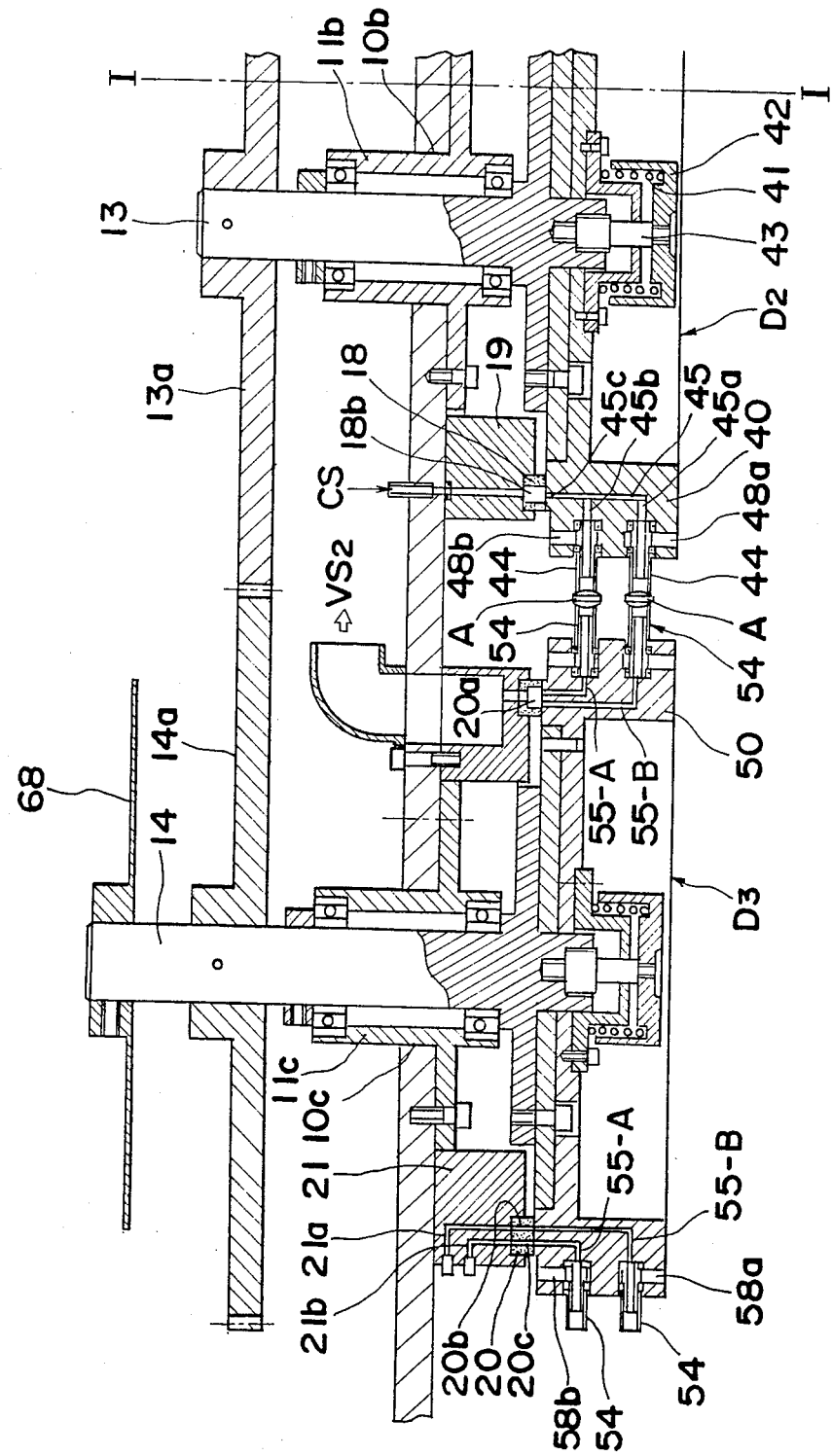
FIG. 2, comprised of FIGS. 2(a) and 2(b), is a cross-sectional view taken along the line II—II in FIG. 1.

Referring still to FIG. 2 comprised of FIGS. 2(a) and 2(b) and illustrating the transporting apparatus in its entirety when FIGS. 2(a) and 2(b) are brought together with the chain line I—I in FIG. 2(a) superposed exactly upon that in FIG. 2(b), the support plate 10 includes annular seal members 16, 18 and 20 each made of a low frictional synthetic material. These annular seal members 16, 18 and 20 are carried by the support plate 10 in concentrical relation to the bores 10a, 10b and 10c through solid ring members 17, 19 and 21, respectively, which ring members 17, 19 and 21 are rigidly secured to the support plate 10. To permit each of the annular seal members 16, 18 and 20 to be supported by the associated ring member 17, 19 or 21, the ring member 17, 19 or 21 may have an annular recess defined therein for receiving the respective seal member 16, 18 or 20 which may be pressure-fitted thereto. For a purpose which will become clear from the subsequent description, and as shown by the phantom lines in FIG. 1, the seal member 16 has defined therein first and second suction slots 16a and 16c fluid-connected to a first source VS1 of vacuum of, for example, 50 to 150 mmHg and a second source VS2 of vacuum of, for example, 100 to 500mmH$_2$O, respectively, through associated openings in the ring member 17 and the support plate 10, and also first and second blow slots 16b and 16d fluid-connected to a common source CS of compressed air of, for example, 0.05 kg/cm$^2$ through associated openings in the ring member 17 and the support plate 10; said first blow slot 16b being positioned between the first and second suction slots 16a and 16c and said second blow slot 16c being positioned adjacent one of the opposite ends of the second suction slot 16c remote from the first blow slot 16b. Similarly, the seal member 18 has defined therein a suction slot 18a and a blow slot 18b fluid-connected to the second vacuum source VS2 and the compressed air source CS, respectively, through associated openings in the ring member 19 and the support plate 10. The seal member 20 has defined therein a suction slot 20a fluid-connected to the second vacuum source VS2 through associated openings in the ring member 21 and the support plate 10, and also first and second blow slots 20b and 20c fluid-connected to the compressed air source CS through a fluid switching circuit which will be described later by means of associated passages 21a and 21b defined in the ring member 21, said first and second blow slots 20b and 20c being positioned side-by-side adjacent one of the opposite ends of the suction slot 20a on the leading side with respect to the direction of rotation of the delivery drum D3.

Specifically, the first blow slot 16b and the second blow slot 16d both in the seal member 16, should be positioned immediately above the shaft 12 and at a location corresponding to the first transfer station, respectively, while the first suction slot 16a extends circumferentially on one side of the first blow slot 16b opposite to the second suction slot 16c and, with respect to the direction of rotation of the supply drum D1, on the trailing side. Similarly, the suction slot 18a in the seal member 18 extends circumferentially from a location corresponding to the first transfer station to a location preceding the blow slot 18b, which is positioned at a location corresponding to the second transfer station, in a direction conforming to the direction of rotation of the intermediate drum D2. The suction slot 20a in the seal member 20 extends angularly from a location corresponding to the second transfer station to a location preceding both of the first and second blow slots 20b and 20c, which are positioned at a location corresponding to the sorting station, in a direction conforming to the direction of rotation of the delivery drum D3.

It is to be noted that, in the practice of the present invention, the use of the seal members 16, 18 and 20 may not be always essential and, where they are not employed, the requisite slots may be formed in the associated ring members 17, 19 and 21. In addition, the ring members 17, 19 and 21 may be an integral part of the support plate 10.

Hereinafter, the constituent units of the transporting apparatus will be described in detail separately under the respective headings.

Hopper Assembly A

Referring to FIG. 1, the supply hopper assembly H as shown includes a batch tank 22 carried by the support plate 10 and having its bottom opening communicated with a supply hopper 23 so that a batch of the products accommodated within the batch tank 22 can fall by gravity into the hopper 23 positioned beneath the batch tank 22. The hopper 23 is of a generally triangular box-like configuration and has its interior divided by a damper plate 24 into rear and front chambers 23a and 23b, the rear chamber 23a being in communication with the batch tank 22 and the front chamber 23b partly overhanging the supply drum D1 with a portion of said drum D1 movably accommodated therein. The hopper 23 has a bottom plate 25 so inclined downwardly towards the supply drum D1 that the solid products A within the rear chamber 23a can slide and roll by gravity downwardly along the bottom plate 25 towards the front chamber 23b through a controlled opening between the damper plate 24 and the bottom plate 25. The bottom plate 25 has a nozzle assembly 26 secured thereto at a position adjacent the outer periphery of the supply drum D1 for jetting compressed air of, for example, about 1.5 kg/cm$^2$ from a compressed air source CS1 into the front chamber 23b so that the solid products A within the front chamber 23b can be lifted in air so as to assume a velocity generally matching with the peripheral velocity of the supply drum D1 for the purpose of enabling the products A to be readily carried by the supply drum D1 being then rotated as will be described later in connection with the supply drum D1.

The hopper assembly H also includes trailing and leading sets 27a and 27b of paired positioning rollers all made of rubber or a similar soft and elastic material and mounted on respective shafts for free eccentric movement in all directions perpendicular to these respective shafts, and a nozzle assembly 28 for jetting compressed air of, for example, about 0.3 kg/cm$^2$ from a compressed air source CS2 into the front chamber 23b in the direction of rotation of the supply drum D1. The function of each of the elements 27a, 27b and 28 will be described later in connection with the supply drum D1.

Supply Drum D1

Figure 3:
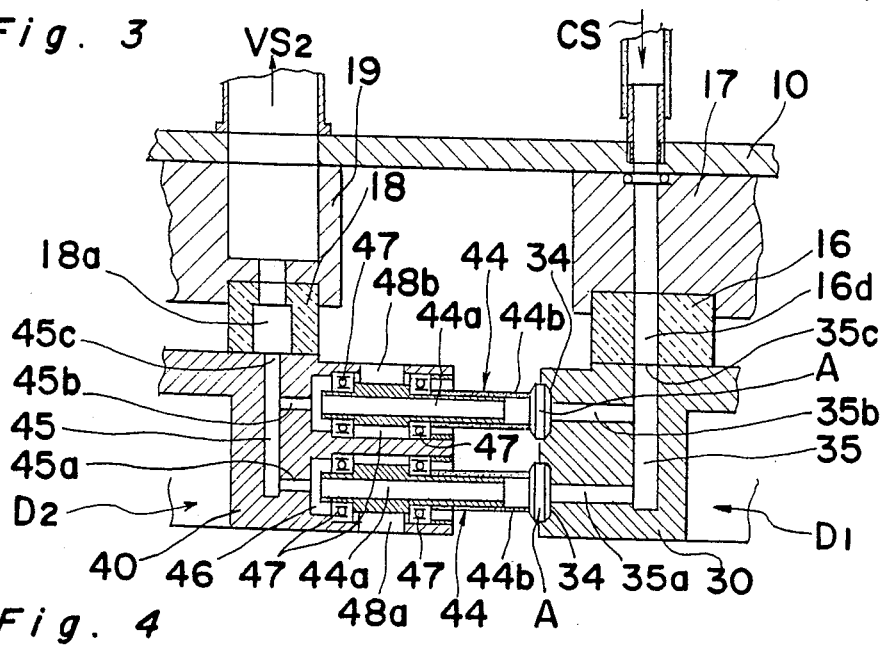
FIGS. 3 and 4 are sectional views, on an enlarged scale, showing the transfer of the products from the supply drum onto the intermediate drum at the first transfer station and that from the intermediate drum onto the delivery drum at the second transfer station, respectively.

Referring to FIGS. 1, 2(a) and 3, the supply drum D1 is of a construction having its outer periphery delimited by a cylindrical wall 30 integral therewith and extending in parallel relation to the shaft 12. This drum D1 is mounted on the shaft 12 for rotation together therewith as hereinbefore described and is elastically urged axially inwardly of the shaft 12 by a compression spring 31 interposed between the drum D1 and a cap member 32, said cap member 32 being axially displaceably secured to the shaft 12 by means of a bolt 33 which is threaded to the shaft 12. With the drum D1 so urged by the compression spring 31, one of the opposite annular end faces of the cylindrical wall 30 adjacent the seal member 16 is held in sliding contact with said seal member 16.

As illustrated, the supply drum D1 has circumferentially extending outer and inner rows of radially inwardly recessed pockets 34 which are defined in the outer peripheral surface of the cylindrical wall 30 so as to open radially outwards in circumferentially equally spaced relation to each other. The cylindrical wall 30 is formed therein with generally F-shaped passages 35 equal in number to the pockets 34 in one circumferential row and having first, second and third open ends 35a, 35b and 35c which open at the bottoms of the associated pockets 34 in the outer row, the bottoms of the associated pockets 34 in the inner row and the annular end face of the cylindrical wall 30 adjacent the seal member 16, respectively, it being to be understood that the third open ends 35c of all of the passages 35 are arranged in a circle concentric with the shaft 12 and open at the annular end face of the cylindrical wall 30 for selective communication with any one of the slots 16a to 16d in the seal member 16.

These F-shaped passages 35 are adapted to be, during each complete rotation of the supply drum D1, communicated selectively with the first vacuum source VS1 through the first suction slot 16a, then with the compressed air source CS through the first blow slot 16b, with the second vacuum source VS2 through the second suction slot 16c, and finally with the compressed air source CS through the second blow slot 16d. Thus, it will readily be seen that, during each complete rotation of the supply drum D1, each of the pockets 34 in any one of the outer and inner rows can be sequentially communicated with the first vacuum source VS1 to receive the respective product A from the hopper 23; with the compressed air source CS to effect centering of the product so received in the respective pocket 34, i.e., to accurately position the received product within the respective pocket 34 by allowing the product to instantaneously pop up by the effect of a blast of compressed air; with the vacuum source VS2 to hold the product in position within the respective pocket 34 after the centering and until it is transported to the first transfer station; and again with the compressed air source CS to blow the product off from the respective pocket 34 for the transfer onto the intermediate drum D2 at the first transfer station.

While the products A are successively tranported from the supply station towards the first transfer station carried by the supply drum D1 in the manner hereinbefore described, it may happen that, depending on the type of the products, some of the products A will be sucked into, and held by, the respective pockets 34 in the wrong position. The products received in the respective pockets 34 in the wrong position can successively be corrected into the right position as they pass underneath the trailing and leading sets 27a and 27b of the rollers which serve to regulate the height of each product that projects outwardly from the respective pocket 34. On the other hand, the nozzle assembly 28 serves to remove some of the products, which are carried by the drum D1 without being regularly seated in the respective pockets 34, from the outer peripheral surface of the cylindrical wall 30 by applying the continued blast of compressed air.

Intermediate Drum D2

Referring to FIGS. 1, 2, 3 and 4, the intermediate drum D2 is of a configuration having its outer periphery delimited by a cylindrical wall 40 integral therewith and extending in parallel relation to the shaft 13. In a manner similar to the supply drum D1, this drum D2 is mounted on the shaft 13 for rotation together therewith as hereinbefore described and is elastically urged axially inwardly of the shaft 13 by a compression spring 41 interposed between the drum D2 and a cap member 42, said cap member 42 being axially displaceably secured to the shaft 13 by means of a bolt 43 which is threaded to the shaft 13. With the drum D2 so urged by the compression spring 41, one of the opposite annular end faces of the cylindrical wall 40 adjacent the seal member 18 is held in sliding contact with said seal member 18.

The intermediate drum D2 has circumferentially extending outer and inner rows of tubular receptacles 44 which extend radially outwardly from the outer peripheral surface of the cylindrical wall 40 in circumferentially equally spaced relation to each other. The outer and inner rows of the tubular receptacles 44 are spaced a distance equal to the spacing between the outer and inner rows of the pockets 34 in the supply drum D1 such that, at the first transfer station where the drums D1 and D2 are spaced a minimum distance therebetween, the tubular receptacles 44 in the outer and inner rows can be exactly aligned successively with the pockets 34 of the outer and inner rows in the supply drum D1 during the continued rotation of said drums D1 and D2.

Figure 4:
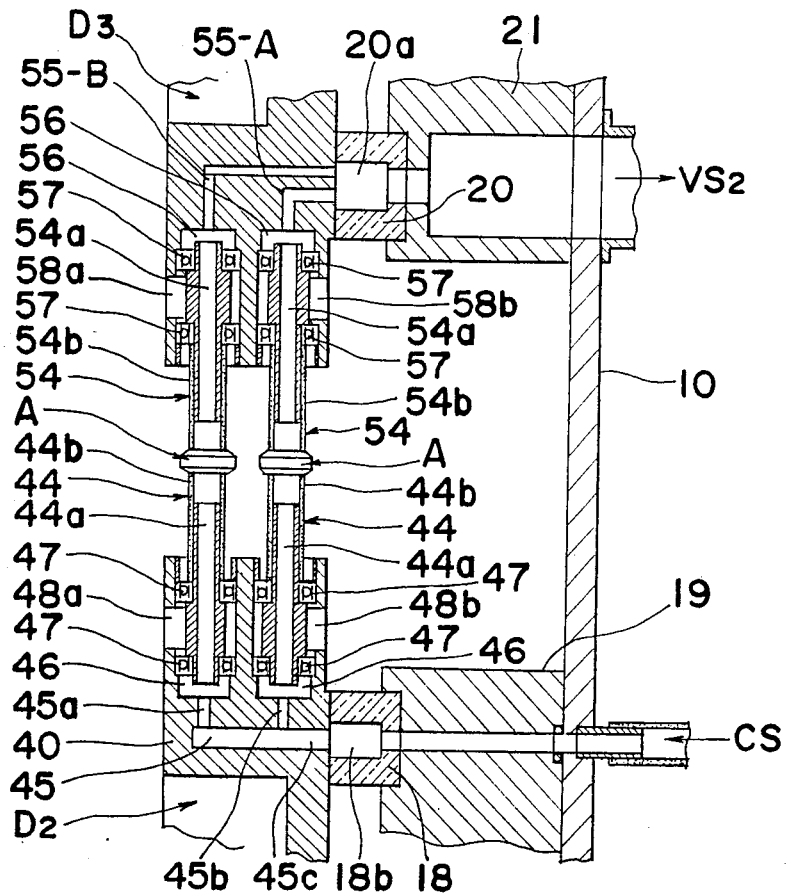

While the manner by which all of the tubular receptacles 44 are supported by the drum D2 will be described later, each of the tubular receptacles in any one of the outer and inner rows is, as best shown in FIGS. 3 and 4, comprised of an inner tube 44a of rigid material such as, for example, metal, having one end received rotatably, but axially non-movably in the cylindrical wall 40, and an outer tube 44b of elastic material such as, for example, rubber, mounted tightly on the opposite end of the inner tube 44a. Each of the tubular receptacles 44 of the construction described above is adapted to be selectively communicated with the vacuum source VS2 and the compressed air source CS respectively through the suction slot 18a and the blow slot 18b both in the seal member 18 and, for this purpose, the cylindrical wall 40 has formed therein generally F-shaped passages 45 equal in number to the tubular receptacles 44 in one circumferential row and having first, second and third open ends 45a, 45b and 45c. While, as is the case with the third open ends 35c of the passages 35 in the supply drum D1, the third open ends 45c of all of the passages 45 are arranged in a circle concentric with the shaft 13 and open at the annular end face of the cylindrical wall 40 for selective communication with any one of the suction and blow slots 18a and 18b in the seal member 18, the first and second open ends 45a and 45b are communicated respectively with the outer and inner rows of the tubular receptacles 44.

In the construction so far described, it is clear that, during each complete rotation of the supply drum D1, each of the tubular receptacles 44 in any one of the outer and inner rows can be sequentially communicated with the second vacuum source VS2 through the suction slot 18a to receive the respective product A released from the associated pocket 34 in the supply drum D1 then communicated with the compressed air source CS, and then with the compressed air source CS through the blow slot 18b to blow the product, which has been transferred thereto from the supply drum D1 and subsequently transported from the first transfer station to the second transfer station, off from the respective tubular receptacle 44 for the transfer onto the delivery drum D3. FIG. 3 illustrates the condition in which the products carried by the pockets 34 of the outer and inner row in the supply drum D1 are transferred onto the tubular receptacles 44 of the corresponding outer and inner rows in the intermediate drum D3, whereas FIG. 4 illustrates the condition in which the products carried by the tubular receptacles of the outer and inner rows in the intermediate drum D2 are transferred onto similar tubular receptacles of the corresponding outer and inner rows in the delivery drum D3 as will be subsequently described.

In order to ensure that, at the first transfer station, each of the tubular receptacles 44 can without fail receive the respective product A upon the communication with the vacuum source VS2, each outer tube 44b mounted tightly on the respective inner tube 44a preferably has its free end terminating at such a location that, upon the contact with the corresponding product carried by the associated pocket 34 and arriving at the first transfer station, the outer tube 44b can be axially inwardly compressed a predetermined slight distance, for example, about 0.2 mm.

As best shown in FIGS. 3 and 4, the cylindrical wall 40 has defined therein pairs of juxtaposed recesses 46 one for each tubular receptacle 44 in the outer row and the other for each tubular receptacle 44 in the inner row, each of said recesses 46 extending radially inwardly from the outer peripheral surface of the cylindrical wall 40 into the body of the wall 40 and terminating in communication with the respective first or second open end 45a or 45b of the associated passage 45 in the intermediate drum D2. The inner tubes 44a of the tubular receptacles 44 in any one of the outer and inner rows are rotatably, but axially nonmovably inserted into the respective recesses 46 and held in position by means of bearings generally identified by 47 and pressure-fitted into such recesses 46. In addition, the opposite annular end faces of the cylindrical wall 40 being of an outer diameter greater than the outer diameter of the seal member 18 is provided with front and rear annular grooves 48a and 48b each concentric with the shaft 13, the front annular groove 48a communicated with the recesses 46 for the outer row of the tubular receptacles 44 on the one hand and open laterally towards the support plate 10 on the other hand whereas the rear annular groove 48b is communicated with the recesses 46 for the inner row of the tubular receptacles 44 on the one hand and open laterally in a direction opposite to the support plate 10 on the other hand.

At appropriate positions covered by the illuminator units I1 and I2, respectively, spinners are provided for engagement with the inner tubes 44a of the outer and inner rows of the tubular receptacles 44, respectively, for spinning the tubular receptacles 44 about their own longitudinal axes. The details of the spinners will be described later with particular reference to FIGS. 7 to 12 under the heading of "Spinning System".

Delivery Drum D3

Referring to FIGS. 1, 2(b) and 4 to 6, the delivery drum D2 is of a configuration having its outer periphery delimited by a cylindrical wall 50 integral therewith and extending in parallel relation to the shaft 14. This delivery drum D3 mounted on the shaft 14 for rotation together therewith is elastically urged axially inwardly of the shaft 14 by a compression spring 51 interposed between the drum D3 and a cap member 52, said cap member 52 being axially displaceably secured to the shaft 14 by means of a bolt 53 which is threaded to the shaft 14. With the drum D3 so urged by the compression spring 51, one of the opposite annular end faces of the cylindrical wall 50 adjacent the seal member 20 is held in sliding contact with said seal member 18.

The delivery drum D3 so supported in the manner as hereinabove described is of a construction identical with the intermediate drum D2 and, therefore, while the details thereof will not be described for the sake of brevity, has elements 54, 54a, 54b, 56, 57, 58a and 58b which correspond in structure and function to the tubular receptacles 44, the inner tubes 44a, the outer tubes 44b, the recesses 46, the bearings 47, the front annular groove 48a and the rear annular groove 48b all employed in the intermediate drum D2. However, the delivery drum D3 differs in structure from the intermediate drum D2 in that, while the intermediate drum D2 employs the generally F-shaped passages 45 each having the first, second and third open ends 45a, 45b and 45c, the delivery drum D3 employs separate passages 55-A and 55-B of generally L-shaped configuration, the passages 55-A being communicated at one end with the outer row of the tubular receptacles 54 and at the opposite end opening at the annular end face of the cylindrical wall 50 for communication with either the suction slot 20a and the first blow slot 20c while the passages 55-B are communicated at one end with the inner row of the tubular receptacles 54 and at the opposite end opening at the annular end face of the cylindrical wall 50 in side-by-side relation to the other ends of the passages 55-A for communication with either the suction slot 20a or the second blow slot 20b.

Figure 5:
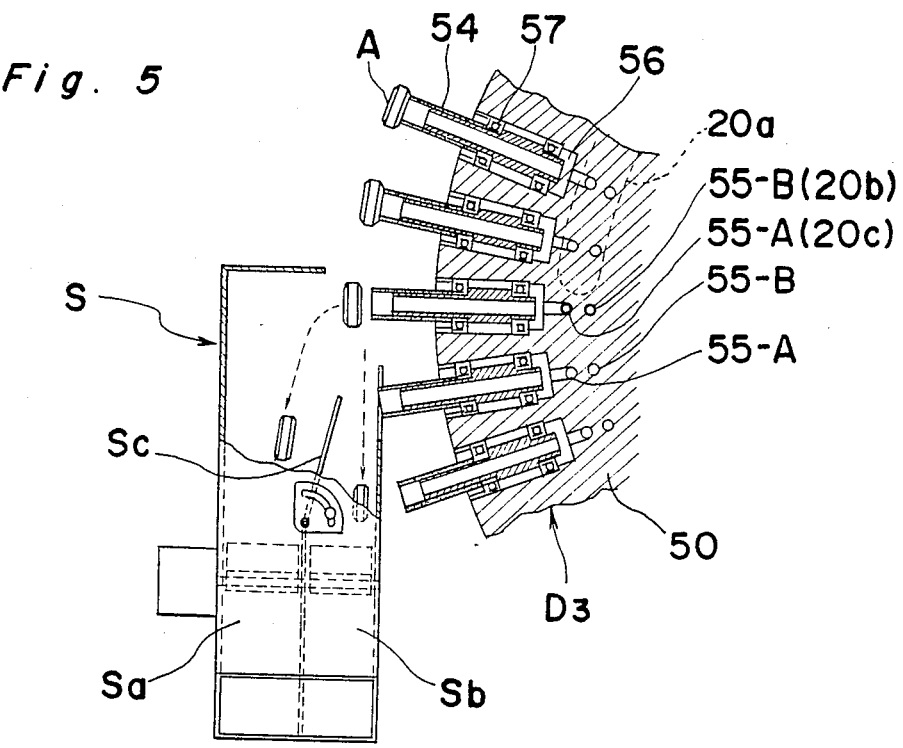
FIG. 5 is a sectional view, on an enlarged scale, showing the manner by which the products are sorted at the sorting station.

With the delivery drum D3 constructed as hereinbefore described, it is clear that, during each complete rotation of the delivery drum D3, each of the tubular receptacles 54 in either the outer and inner row can be sequentially communicated with the second vacuum source VS2 through the suction slot 20a to receive the respective product A released from the associated tubular receptacle 44 in the intermediate drum D2 then communicated with the compressed air source CS, as shown in FIG. 4, and then with the compressed air source CS through the first or second blow slot 20b or 20c to blow the product, which has been transferred thereto from the intermediate drum D2 and subsequently transported from the second transfer station to the sorting station, off from the respective tubular receptacle 54 onto the sorting box S, as shown in FIG. 5.

Figure 6:
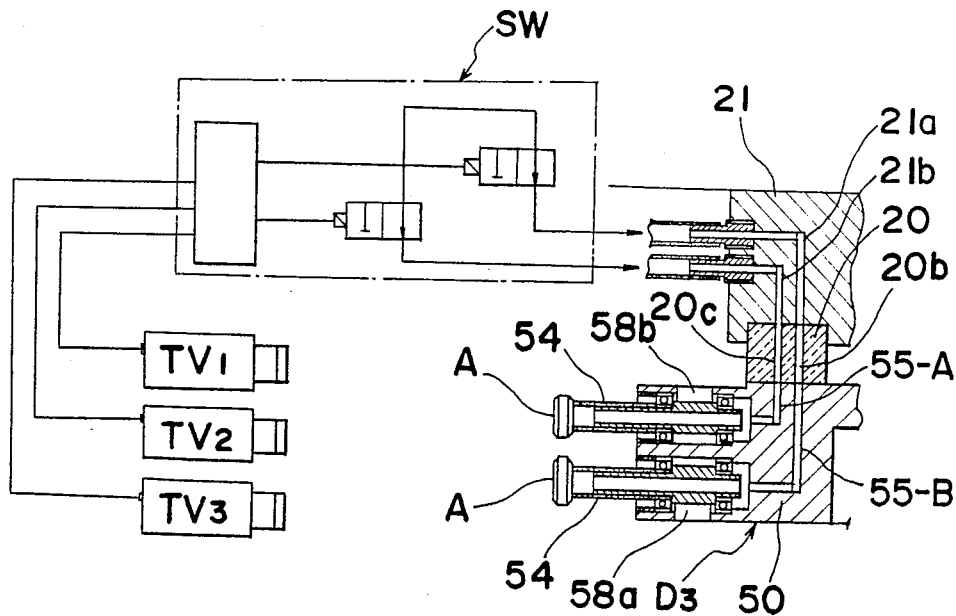
FIG. 6 is a diagram showing the relationship between the tubular receptacles arriving at the sorting station and a fluid switching circuit operable under the control of television cameras.

Depending upon the result of inspection done by any one of the television cameras TV1, TV2 and TV3, all electrically connected to the fluid switching circuit generally identified by SW in FIG. 6, one or both of the passages 21b and 21a in the ring member 21, which are adapted to be communicated with the passages 55-A and 55-B in the delivery drum D3 through the second and first blow slots 20c and 20b, respectively, are disconnected from the compressed air source. Specifically, if the result of inspection done by all of the television cameras TV1, TV2 and TV3 shows that no flaw is present in all of the products, both of the passages 55-A and 55-B are communicated with the compressed air source CS to blow the products A so that they can fall into one of the two ducts Sa and Sb of the sorting box S which is assigned to receive all of the acceptable products, as shown in FIG. 5. However, if at least one of the television cameras has indicated that one product contains a flaw, the fluid switching circuit SW disconnects from the compressed air source CS only the passage 55-A or 55-B associated with the tubular receptacle 44 or 54 which has carried such products, and accordingly, the product containing the flaw is, without being blown off from the tubular receptacle 54, forced to fall by gravity into the other duct Sb of the sorting box S which is assigned to receive all of the rejected products. For the purpose of guiding the products into any one of the ducts Sa and Sb, the sorter box S has an adjustable deflector Sc as best shown in FIG. 5.

As best shown in FIG. 1, the duct Sa of the sorting box S is communicated to a delivery conveyor 100 for the conveyance to the subsequent processing station while the duct Sb may be communicated to any suitable recovery box (not shown).

SPINNING SYSTEM

Figure 7:
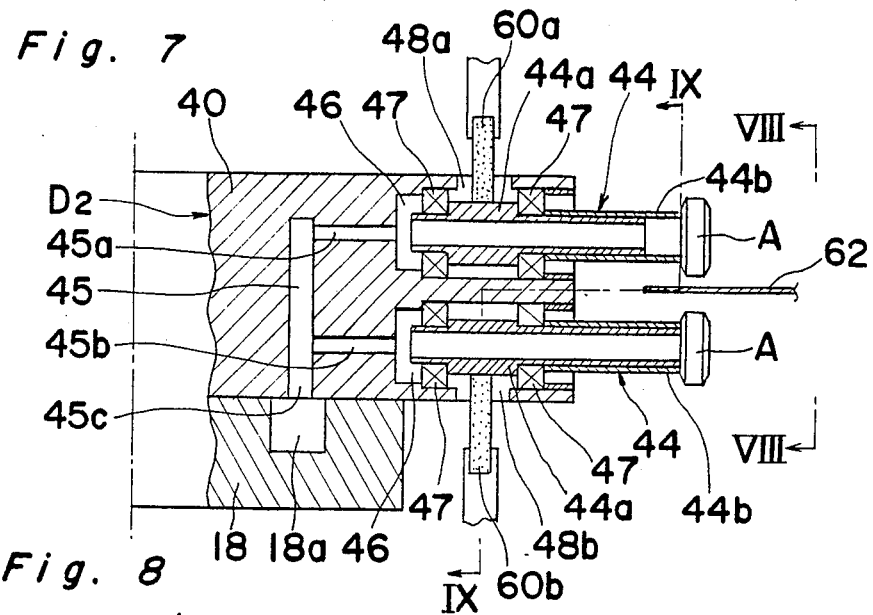
FIG. 7 is a sectional view, on an enlarged scale showing spinners for spinning the tubular receptacles in any one of the intermediate and delivery drums.
Figure 8:
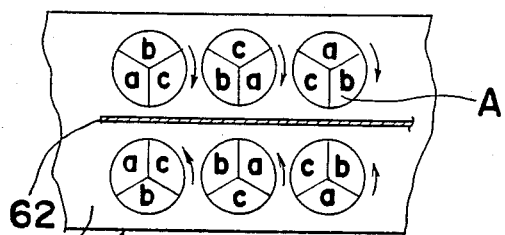
FIG. 8 is a top plan view of a portion of the intermediate or delivery drum showing how the surface of each of the products being transported can be illuminated when the respective product is spun, as viewed in a direction shown by the chain line VIII—VIII in FIG. 7.
Figure 9:
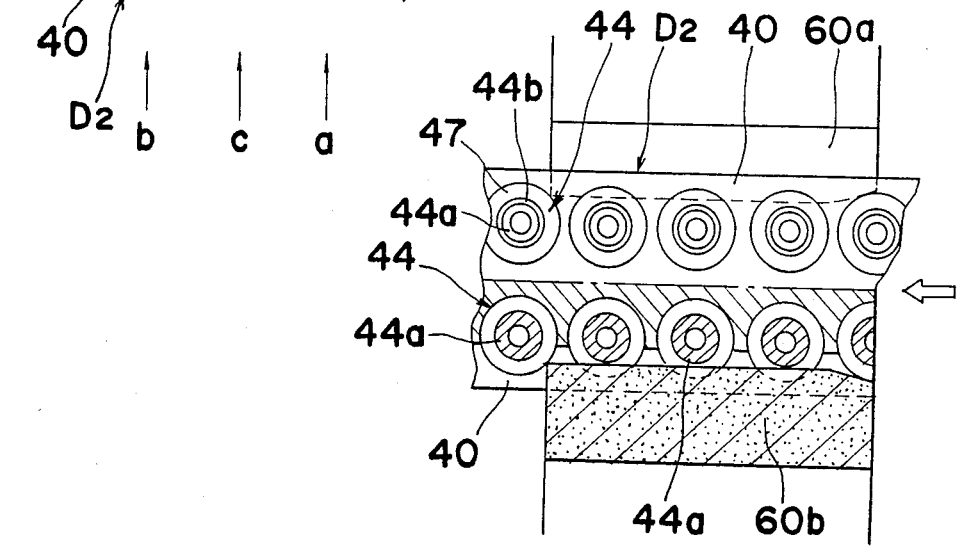
FIG. 9 is a partly sectional area taken along the line IX—IX shown in FIG. 7.

Referring now to FIGS. 7 to 13, particularly to FIGS. 7 to 9, the spinning systems for the intermediate drum D2 and that for the delivery drum D3 are identical in structure and function with one another and, accordingly, only the spinning system associated with the intermediate drum D2 will be described for the sake of brevity. At the position covered by the illuminator unit I1 shown in FIG. 1, the spinners are provided laterally inwardly and outwardly of the cylindrical wall 40 for engagement with the inner tubes 44a of the outer and inner rows of the tubular receptacles 44 to spin the latter in one direction about their own longitudinal axes. The spinners as shown in FIGS. 7 to 9 comprise front and rear friction bands 60a and 60b fixedly supported by the support plate 10 and partially protrude into the respective grooves 48a and 48b from opposite directions so that, as the drum D2 rotates in one direction about the shaft 13, the inner tubes 44a of the respective outer and inner rows of the tubular receptacles 44 can contact the front and rear friction bands 60a and 60b, spinning about their own axes. Each of the friction bands 60a and 60b is of such a length that the inner tube 44a and, hence, the tubular receptacle 44 then contacting the respective friction band 60a or 60b can undergo at least one complete rotation about its own axis during the passage thereof within the associated inspecting zone covered by the angle of view of the associated television camera TV1.

Figure 10:
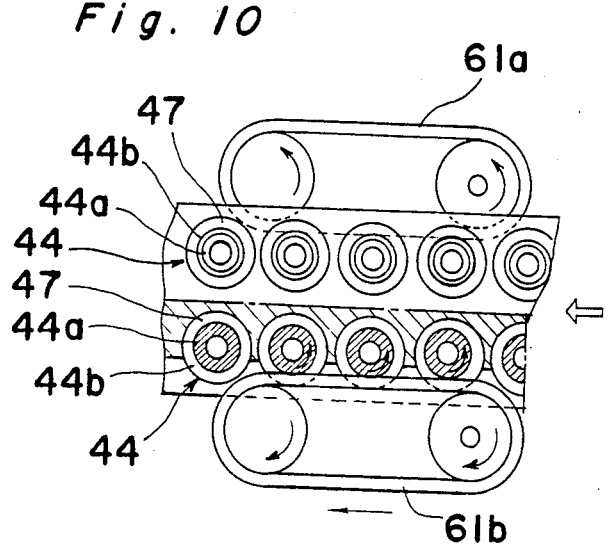
FIG. 10 is a view similar to FIG. 9, showing a modification of the spinners shown in FIGS. 7 and 9.

Alternatively, as shown in FIG. 10, the spinners may comprise front and rear endless belts 61a and 61b each trained between drive and driven pulleys supported laterally of the cylindrical wall 40 and partially protruding into the respective annular groove 48a or 48b for engagement with the inner tubes 44a in the associated row.

As best shown in FIG. 8, because the tubular receptacles 44 are rotated about their own longitudinal axes in contact with the corresponding spinners during the rotation of the drum D2, the entire surface of each of the products then being transported by the tubular receptacles 44 can be viewed by the television camera. This is particularly true where the illuminator unit emits rays of light in a direction slantwise relative to each product in such a quantity as to illuminate about one third of the entire surface of each product such as shown by a, b and c in FIG. 8. In other words, as each tubular receptacle 44 is rotated about its own longitudinal axis, the position of the surface area a moves to the position which has been occupied by the surface area b, which position of the surface area b moves to the position which has been occupied by the surface area c, with the surface area c consequently occupying the position which has been occupied by the surface area a. Thus, all of the surface areas of each product can successively exposed to the illuminator unit.

The above description equally applies to the spinners positioned within the inspecting zone covered by the angle of view of the television camera TV2 adjacent the delivery drum D3. However, when it comes to the spinners positioned within the inspecting zone covered by the angle of view of the television camera TV3 assigned to inspect the peripheral face of each product, reference should be made to FIGS. 12 and 13.

In FIGS. 7 and 8, reference numeral 62 designates a light shield for avoiding any possible interference between rays of light projected towards the outer row of the tubular receptacles and that towards the inner row of the tubular receptacles. The use of this light shield 62 is necessary where a single television camera TV3 is employed for inspecting the peripheral faces of the respective products which are positioned in side-by-side relation with respect to the circumferential direction of the delivery drum D3.

Figure 11A:
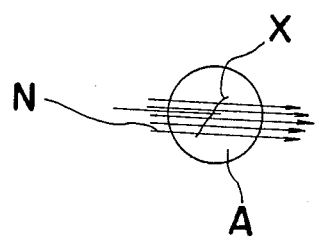
FIGS. 11(a) and 11(b) are schematic top plan view of the product being scanned by a television camera shown in relation to the scan lines.
Figure 11B:
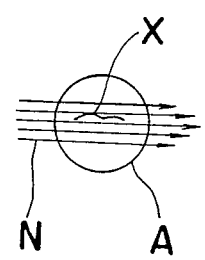
Figure 12:
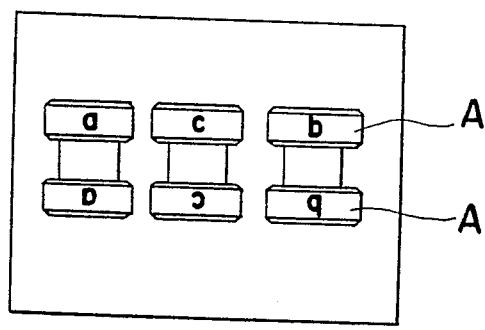
FIG. 12 is a side view of the products being passed across a third inspecting zone while being spun about their axes.
Figure 13:
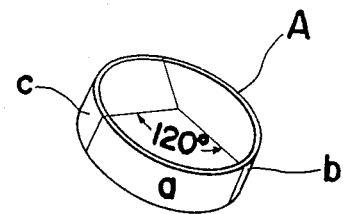
FIG. 13 is a perspective view, on an enlarged scale, showing the product in the form of a tablet.

The use of the spinners brings about an additional advantage. In the event that the product being inspected contains a crack shown by X and that the defective product is allowed to pass across the inspecting zone in a position with the crack X extending in a direction generally parallel to the scan lines N of the television camera TV1 or TV2, it is clear that the accuracy of the detection of the presence of the crack X will be adversely affected and a monitor television receiver set will fail to show the presence of the crack X on the product. This possibility can advantageously be eliminated if the product is rotated together with the associated tubular receptacle as shown in FIG. 11(a) showing that the crack X which extended generally in parallel to the direction of the scan lines N has been turned to extend generally at an angle to the direction of the scan lines N.

Figure 14:
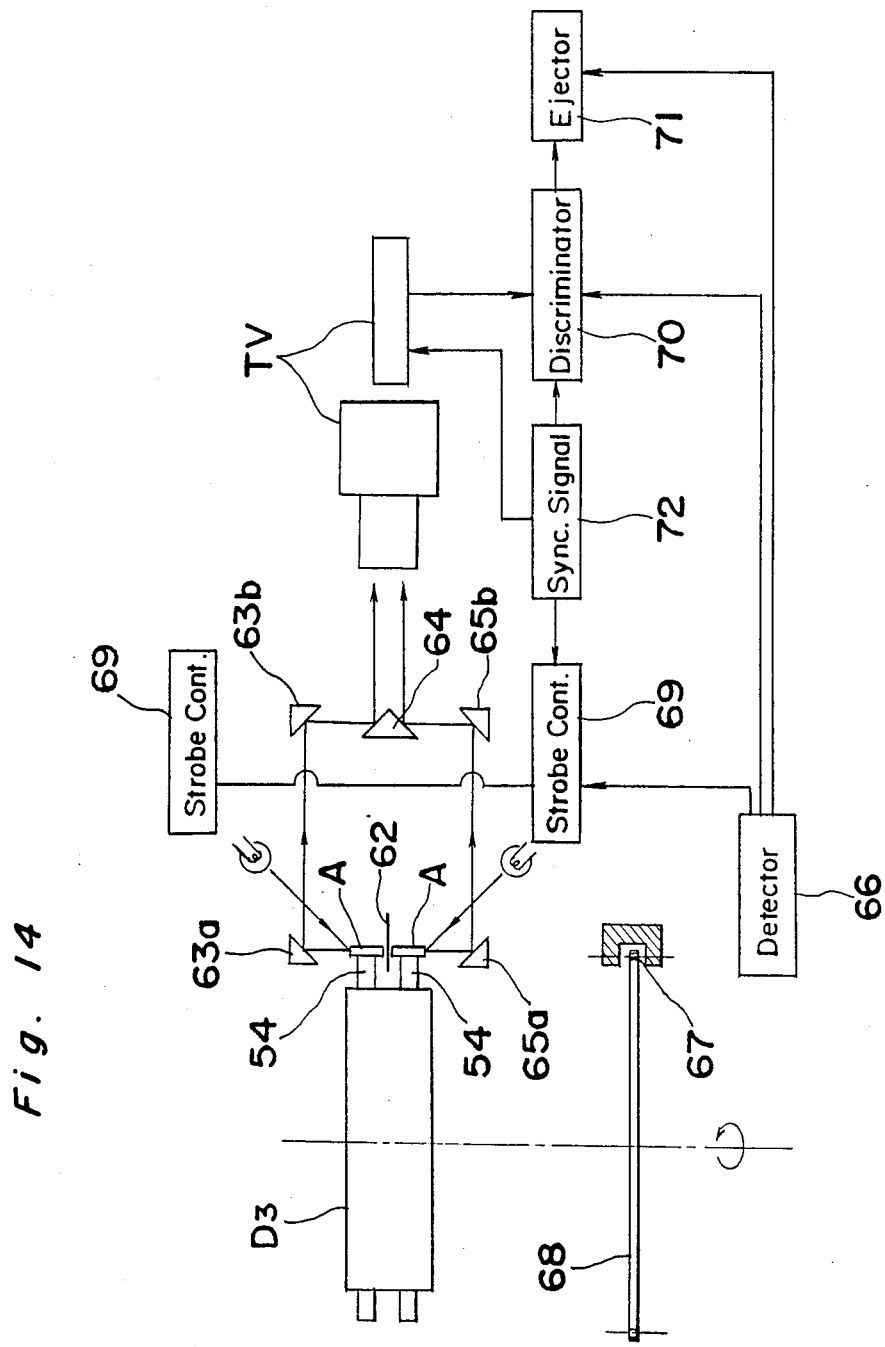
FIG. 14 is a schematic block circuit diagram showing a television camera for inspecting the peripheral face of each product and its related circuit.

TELEVISION INSPECTING SYSTEM

Where the delivery drum D3 is provided with the outer and inner rows of the tubular receptacles 54, which rows are arranged in side-by-side relation to each other in a direction parallel to the longitudinal axis of the shaft 14, it is possible to inspect both the peripheral face of the product carried by the respective receptacle 44 in the outer row and that in the inner row by the use of only a single television camera TV in a manner as shown in FIG. 14. Referring now to FIG. 14, an image of the peripheral face of each product carried by the tubular receptacle 54 in the outer row is adapted to be transmitted to the television camera TV through a plurality of prism mirrors 63a and 63b and a common prism mirror 64 while an image of the peripheral face of each product carried by the tubular receptacle 54 in the inner row is adapted to be transmitted to the television camera TV through a corresponding number of prism mirrors 65a and 65b and the common prism mirror 64. The circuit shown in FIG. 14 utilizes a position detecting circuit 66 for detecting the passage of a particular hole 67 defined in a synchro-disc 68 rigidly mounted on the shaft 14 for rotation together therewith, strobe firing circuits 69 adapted to be controlled by the position detecting circuit 66, a discriminating circuit 70, an ejector control 71 and a synchronizing signal circuit 72 for controlling the television camera TV.

In the construction described hereinbefore, the product transporting apparatus according to the present invention operates in the following manner. Assuming that the supply, intermediate and delivery drums D1, D2 and D3 are driven by the motor M in synchronism with each other, some products A within the supply hopper 23 are successively sucked into and received in the pockets 34 on the supply drum D1 then communicated with the vacuum source VS1. As each of the pockets 34 carrying the products A therein approaches the top position immediately above the shaft 12, the pockets 34 are successively communicated with the compressed air source CS through the first blow slot 16b while the communication thereof with the vacuum source VS1 is immediately interrupted. Upon communication between each pocket 34 and the compressed air source CS, the respective product received in such pocket 34 is floated in air for the centering thereof relative to such pocket 34. Immediately after the centering, the associated pocket 34 becomes discommunicated from the compressed air source CS and communicated with the vacuum source VS1 through the second suction slot 16c whereby the product once floated in air for the centering purpose is immediately seated in such pocket 34 until it arrives at the first transfer position.

Subsequent communication between each pocket 34 and the compressed air source CS through the second blow slot 16d permits the corresponding product to be fed onto one of the tubular receptacles 44 on the intermediate drum I2 which is then communicated with the vacuum source VS2 through the suction slot 18a. In this way the products transported by the supply drum D1 from the supply station to the first transfer station are successively transferred onto the corresponding tubular receptacles 44 on the intermediate drum D2.

The products A so transferred onto the intermediate drum D2 are then transported towards the second transfer position while sucked in and retained by the corresponding tubular receptacles 44 then communicated with the vacuum source VS2 through the suction slot 18a. Upon arrival at the second transfer position, the products are successively transferred from the corresponding tubular receptacles 44, then communicated with the compressed air source CS through the blow slot 18b, onto the associated tubular receptacles 54 on the delivery drum D3 which are then communicated with the vacuum source VS2 through the common suction slot 20a. The products transferred successively onto the corresponding tubular receptacles 54 on the delivery drum D3 are sucked into and retained by such corresponding receptacles 54 until they arrive at the sorting station at which the tubular receptacles 54 are communicated selectively with the compressed air source depending on the result of inspection performed by the television cameras TV1, TV2 and TV3 as hereinbefore described.

Figure 20A:
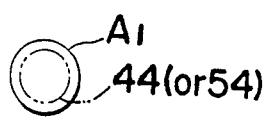
FIGS. 20(a) to 20(i) are top plan views showing various types of the products with which the apparatus can operate.
Figure 20B:
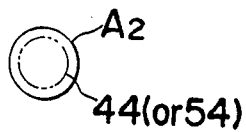
Figure 20C:
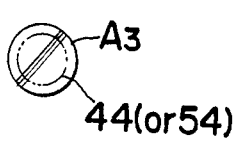
Figure 20D:
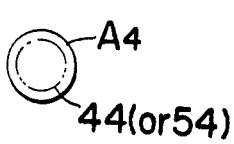
Figure 20E:
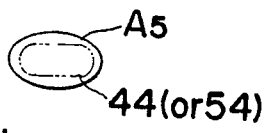
Figure 20F:
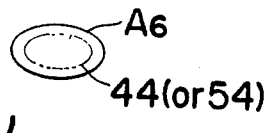
Figure 20G:
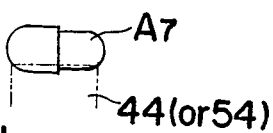
Figure 20H:
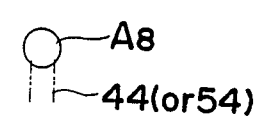
Figure 20I:
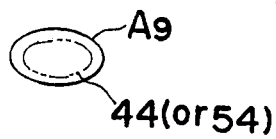
Figure 21A:
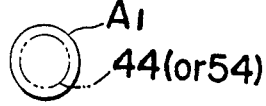
FIGS. 21(a) to 21(i) are side views of the various types of the products shown in FIGS. 20(a) to 20(h), respectively.
Figure 21B:
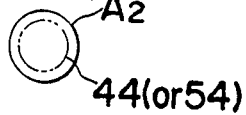
Figure 21C:
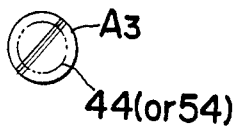
Figure 21D:
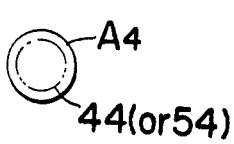
Figure 21E:
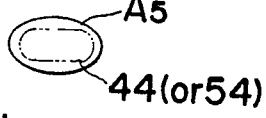
Figure 21F:
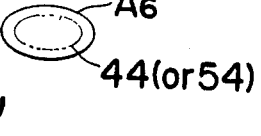
Figure 21G:
Figure 21H:
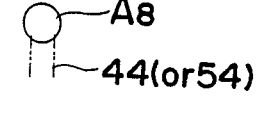
Figure 21I:

In practice, the products A with which the transporting apparatus according to the present invention can handle include, among other products, sugar coated tablets such as shown at A1 in FIGS. 20(a) and 21(a); film-coated tablets such as shown at A2, A4, A5 and A9 in FIGS. 20(b) and 21(b), FIGS. 20(d) and 21(d), FIGS. 20(e) and 21(e) and FIGS. 20(i) and 21(i), respectively; bare tablets such as shown at A5 in FIGS. 20(e) and 21(e); ellipsoidal tablets such as shown at A6 in FIGS. 20(f) and 21(f); hard capsules such as shown at A7 in FIGS. 20(g) and 21(g); and pills such as shown at A8 in FIGS. 20(h) and 21(h). Accordingly, each of the tubular receptacles on any one of the intermediate and delivery drums D2 and D3 must have, as shown by the chain lines in FIGS. 20(a) and 21(a) to FIGS. 20(i) and 21(i), a shape sufficient and necessary to accommodate the product of a particular shape.

It is to be noted that, so far as the product transporting apparatus itself is concerned, the tubular receptacles 44 and 54 in the intermediate and delivery drums D2 and D3 need not be rotatable about their own longitudinal axes and, in such case, the inner tubes 44a and 54a may be pressure-fitted into the respective recesses 46 and 56. Where the inner tubes 44a and 54a of the tubular receptacles 44 and 54 in the intermediate and delivery drums D2 and D3, respectively, are rigidly mounted on the respective drums so as to project radially outwardly from the associated cylindrical walls 40 and 50, it will readily be conceivable to those skilled in the art that the transporting apparatus can be designed so as to operate with the capsules such as shown in FIGS. 15 or 18. In particular, in FIG. 17(a), the inner tube 44a or 54a is a rigid member while the outer tube 44b or 54b is an elastic member; in FIG. 17(b), both of the inner and outer tubes 44a and 44b, or 55a and 55b, are rigid members, but the outer tube 44b or 55b is axially collapsibly mounted on the inner tube 44a or 54a by means of a spring; and in FIG. 17(c), while the inner tube 44a or 54a is a rigid member, the outer tube 44b or 54b is employed in the form of a deformable skirt.

Moreover, where the tubular receptacles 44 and 54 need not be rotatable, each of the tubular receptacles 44 and 54 may be constructed as shown in FIGS. 19(a) to 19(d). In FIG. 19(a), the tubular receptacle is shown as axially movably supported by, but normally radially outwardly biased by a spring element; in FIG. 19(b), the inner tube 44a or 54a is pressure fitted into the cylindrical wall 40 or 50 while the outer tube 44b or 54b mounted on the inner tube is in the form of a bellows; in FIG. 19(c), while the rigid inner tube is pressure-fitted into the cylindrical wall, the elastic outer tube mounted on the inner tube is in the form of a generally trumpet-shaped member; and in FIG. 19(d), the tubular receptacle is axially, displaceably mounted on the cylindrical wall which is made of an elastic material.

Although the present invention has fully been described in connection with the preferred embodiment thereof with reference to the accompanying drawings, it is to be noted that various changes and modifications are apparent to those skilled in the art. By way of example, the number of the rows of the pockets 34 in the supply drum D1 may not be always limited to two such as shown and described, but as least one row may suffice. This also applies to the number of the rows of the tubular receptacles on any one of the intermediate and delivery drums.

Accordingly, Such changes and modifications are to be understood as included within the true scope of the present invention as defined by the appended claims unless they depart therefrom.

What is claimed is:

1. A product transporting apparatus for transporting solid products of generally similar shape and/or size successively from a take-in station towards a take-out station, which comprises, in combination:

a support structure;

at least first and second rotary drums rotatably carried by said support structure for rotation in the opposite directions with respect to each other, and positioned adjacent each other, the point where they are closest being a transfer position, each of said first and second rotary drums having on the peripheral surface a plurality of radially outwardly extending tubular receptacles which are arranged in at least one circumferentially extending row in equally spaced relation to each other, some of said receptacles on the first rotary drum being adapted to successively receive a corresponding number of the products during each rotation of said first rotary drum for transportation of said products from the take-in station towards the transfer position, each of said tubular receptacles on said first and second rotary drums being comprised of an inner tube supported by the associated rotary drum and an outer tube mounted on the inner tube so as to project radially outwardly from the outer periphery of the associated rotary drum, which inner tube is rotatably, but axially non-displaceably inserted into the corresponding outer tube, and bearings on the cylindrical wall of the associated rotary drum holding said inner tubes, and said rotary drum having annular grooves therein concentric with the shaft of the drum, through which said inner tubes are exposed;

a television camera provided on said support structure for inspecting the peripheral faces of the respective products carried by the open end of the outer tube of the respective receptacles;

spinner means supported laterally of the cylindrical wall of said first and second rotary drums and partially protruding into the respective annular grooves for engagement with at least one of the inner tubes of the tubular receptacles to spin the receptacles carrying the product at least one complete rotation about its own axis in one direction during the passage thereof within the associated inspecting zone covered by the angle of view of the television camera; whereby the entire surface of each of the products carried by the receptacles is inspected by the television camera;

means disposed adjacent said first rotary drum at the take-in station for supplying the products one by one onto the receptacles on the first rotary drum;

a source of compressed air;

a vacuum source;

first means for causing said some of the receptacles on the first rotary drum to be successively communicated with the vacuum source for sucking the respective products into said receptacles and also for carrying such products until the products so carried are transported to the transfer position;

second means for causing said some of the receptacles on the first rotary drum to be successively communicated with the compressed air source for blowing the products so transported to the transfer position one by one off the associated receptacles on the first rotary drum;

third means for causing the receptacles on the second drum to be successively communicated with the vacuum source for sucking the respective products released from the corresponding receptacles on the first rotary drum into said tubular receptacles and also for carrying such products until the products so carried are transported to the take-out station; and fourth means for causing the products, which have been successively transported to the take-out station, to be released from the associated receptacles on the second rotary drum onto a subsequent processing station.

2. An apparatus as claimed in claim 1, wherein said outer tube is made of an elastic and soft material.

3. An apparatus as claimed in claim 1, wherein said spinning means comprises a friction band provided for each of the first and second rotary drums for successive engagement with the inner tubes.

4. An apparatus as claimed in claim 1, wherein said spinning means comprises an endless belt adapted to be driven in one direction and provided for each of the first and second rotary drums, said endless belt being engageable successively with the inner tubes.

* * * * *